United States Patent
Hewitt et al.

(10) Patent No.: US 9,480,210 B2
(45) Date of Patent: Nov. 1, 2016

(54) BROCCOLI PLANT AND USE THEREOF

(75) Inventors: John Denison Hewitt, Gilroy, CA (US); Xiaoguang Liang, Beijing (CN); Mathieu Sanvoisin, Les Ponts de Ce (FR); Emmanuel Deschamp, Guyancourt (FR); Jiagang Si, Beijing (CN); Wenhua Lv, Beijing (CN)

(73) Assignee: Syngenta Participations AG, Basel (CH)

( * ) Notice: Subject to any disclaimer, the term of this patent is extended or adjusted under 35 U.S.C. 154(b) by 558 days.

(21) Appl. No.: 13/995,329

(22) PCT Filed: Dec. 15, 2011

(86) PCT No.: PCT/EP2011/072983
§ 371 (c)(1),
(2), (4) Date: Jul. 3, 2013

(87) PCT Pub. No.: WO2012/084702
PCT Pub. Date: Jun. 28, 2012

(65) Prior Publication Data
US 2013/0312140 A1 Nov. 21, 2013

(30) Foreign Application Priority Data

Dec. 21, 2010 (WO) ............... PCT/CN2010/080075

(51) Int. Cl.
*A01H 5/02* (2006.01)
*A01H 5/10* (2006.01)

(52) U.S. Cl.
CPC . *A01H 5/02* (2013.01); *A01H 5/10* (2013.01)

(58) Field of Classification Search
None
See application file for complete search history.

(56) References Cited

U.S. PATENT DOCUMENTS

| 6,667,428 | B1 | 12/2003 | Chen et al. | |
|---|---|---|---|---|
| 7,759,550 | B2 | 7/2010 | Mozsar et al. | |
| 2005/0262594 | A1* | 11/2005 | van den Bosch | A01H 5/00 800/287 |

FOREIGN PATENT DOCUMENTS

| EP | 1597965 | 11/2005 |
|---|---|---|
| WO | 2007062009 | 5/2007 |

OTHER PUBLICATIONS

Machine Harvestable Broccoii, "Tenderstem (R)"; 2013; Retrieved from the Internet: http://www.tenderstem.co.uk/so-tender.php.
International Search Report dated Oct. 13, 2011 for International Patent Application No. PCT/CN2010/080075.
International Preliminary Report on Patentability dated Jun. 25, 2013 for International Patent Application No. PCT/CN2010/080075.
International Search Report dated Feb. 21, 2012 for International Patent Application No. PCT/EP2011/072983.
International Preliminary Report on Patentability dated Jun. 25, 2013 for International Patent Application No. PCT/EP2011/072983.
Baggett, J.R. and Kean, D. Broccoli Breeding Lines OSU 101-OSU 115, Hort. Science, (1985), 20(4):782-784.
Baggett, J.R, and Kean, D. Clubroot-resistant Broccoli Breeding Lines OSU CR-2 to OSU CR-8, Hort. Science. (1985), 20(4): 784-785.

* cited by examiner

*Primary Examiner* — Elizabeth McElwain
(74) *Attorney, Agent, or Firm* — Karen A. Magri

(57) ABSTRACT

The present invention deals with new type of broccoli plant suitable for the industrial manufacture of broccoli heads and florets. The invention relates to broccoli plants producing a head that is flat, comprises multiple individualized florets and protrudes above the leaves making it easy to harvest by machine. The invention further deals with methods and uses of the broccoli plants, heads and florets for the manufacture of broccoli processed and/or packaged food products.

11 Claims, 5 Drawing Sheets

BROCCOLI PLANT AND USE THEREOF

RELATED APPLICATION INFORMATION

This application claims priority under 35 U.S.C. §371 from PCT Application No. PCT/EP2011/072983, filed Dec. 15, 2011, which claims the benefit of PCT Application No. PCT/CN2010/080075, filed Dec. 21, 2010, the disclosures of which are incorporated by reference herein in their entirety.

FIELD OF INVENTION

The present invention deals with plant breeding and more particularly to the development of new broccoli plants adapted for mechanical harvesting and processing for both fresh and frozen industries.

BACKGROUND ART

Broccoli is a member of *Brassica* family like cauliflower and cabbage, its botanic name being *Brassica oleraceae* L. var. *italica*.

Broccoli is native of the Mediterranean region and particularly grown in Italy for centuries. Indeed, it was considered as favorite vegetable by the Romans, who in the beginning ate a purple sprouting broccoli that turned green when cooked.

Broccoli has since been developed by selection and crossing to obtain varieties such as Calabrese (originating from the area of Calabria) or others broccoli varieties which have more and more improved qualities.

Broccoli is high in vitamins C, K, and A, as well as dietary fiber; it also contains multiple nutrients with potent anti-cancer properties, such as diindolylmethane and small amounts of selenium. A single serving provides more than 30 mg of Vitamin C and a half-cup provides 52 mg of Vitamin C. The di-indolylmethane found in broccoli is supposed to be a potent modulator of the innate immune response system with anti-viral, anti-bacterial and anti-cancer activity. Broccoli also contains the compound glucoraphanin, which can be processed into an anti-cancer compound sulforaphane, though the benefits of broccoli may be reduced if the vegetable is boiled more than ten minutes. A high intake of broccoli has been found to reduce the risk of aggressive prostate cancer. Broccoli consumption has also been shown to be beneficial in the prevention of heart disease.

Broccoli is usually boiled or steamed, but may be eaten raw and has become popular as a raw vegetable in hors d'oeuvre trays. Although boiling has been shown to reduce the levels of suspected anti-cancer compounds in broccoli, other preparation methods such as steaming, microwaving, lactic fermentation, and stir-frying have not been shown to reduce the presence of these compounds and so also constitute good alternative ways of cooking broccoli.

Broccoli is mostly marketed and consumed fresh; the part of the plant that is eaten is actually an undeveloped flower head hereinafter named head comprising many tiny buds crowded onto it.

Heads are harvested at maturity when they are an adequate size and have florets with a uniform green color.

A broccoli plant is considered good quality when the head is tight and compact, with a uniform dark green with as little yellowing as possible. A uniform head and floret color is a frequently requested trait in Broccoli. However, "green" head color results from the amount of sunlight reaching the crown of the head and florets. In fact, the yellowing is the result of a decline in chlorophyll (Deschene et al 1991), and is the result of insufficient sunlight exposure by the plant.

Current commercial broccoli varieties have an abundant and high leaf canopy that shades portions of head and this results in a yellowing of part of the head and florets (mainly around outer extremities of the harvested broccolis heads and may extend to individual florets at the center of the crown). This abundant amount of leaves is also an obstacle for the harvesting of the broccoli head.

The most common broccoli varieties grown around the world usually show an average to good vigor, a head height of about 40 to 50 cm above the ground and a leaf canopy height of at about 60 to 70 cm. The color of the head is green—from mild green to deep green—and the shape of the head is convex, i.e. round-shaped with the interior face of the circle oriented toward the ground. The stems of broccoli head are yellow or creamy due to the non exposure to the sunlight. The main stem of the plant holds secondary stems at the extremity of which the florets are arranged on a convex plane—lens-shaped—forming the head.

Broccoli is usually planted at a density of about 30 000 to 40 000 plants per hectare; while at higher density, up to 80 000 plants per hectare can be found. However, the higher the planting density is, the lower the size of the head.

The harvesting of the broccoli head needs to be done at the proper stage of maturity and uniformity of the head and florets. Furthermore, proper handling of the harvested heads and florets is of paramount importance to maintain good organoleptic (texture and color) and nutritional qualities. Indeed the thin buds comprised on the top of the florets constituting the head are very sensitive to crushing, the texture of the florets and stem may rapidly become soft and non appealing and the overall color of the product may also lose its attractiveness.

Due to the architecture of the plant, broccoli harvesting is done manually when the head has reached maturity. The main stem is cut and the head thus obtained is cooled and marketed as fresh product. This manual harvesting is expensive in term of labor cost and may represent up to 60% of the total labor costs for producing broccoli.

The use of mechanical harvesting solutions have been attempted but, because of the importance of leaf content and the deep burying of the head within those leaves, the jamming of the cutting equipment is an issue in the development of any mechanical equipment for harvesting broccoli.

Broccoli is mainly marketed fresh, as fresh heads. There is however a trend for individualized florets packed in bags in order to address a need for convenience and to provide the consumer with ready to eat or ready to cook vegetables.

This kind of packed fresh broccoli florets allows the consumer to cook broccoli conveniently without the need to clean broccoli heads, to cut florets one after the other and eventually to dispose of non-edible broccoli parts.

However, the cost of the processing of broccoli heads for producing individualized florets after harvesting is a serious issue. Indeed, the compactness and the arrangement of the florets forming the head and the convexity of that head make necessary either to manually cut and prepare the florets or to use specifically designed equipment in order to obtain those individualized florets. Moreover, in the current existing broccoli varieties, the uniformity of the florets obtained after processing of the head is not always satisfactory because the secondary stems of the head holding the florets do not have the same length nor the same width and therefore there is a big heterogeneity in the size and caliber of the obtained florets. The length of the secondary stems holding the florets is not uniform and leads to heterogeneous assortment of broccoli florets.

Broccoli is also increasingly marketed as frozen, mainly in the form of individualized florets, either alone or in combination with other vegetables in ready to cook mixes. In those cases as well, there is a need to handle and process the broccoli heads after harvesting as quickly as possible in order to preserve all the organoleptic qualities of the product. Once harvested, the broccoli heads are transported to the freezing factory, then the heads are cleaned, and the florets are cut-out thanks to a specific machine. The thus obtained florets are separated according to their size, the ones that are not conforming to the required standards are usually discarded and the ones of suitable size are kept for bleaching and freezing. The obtained byproducts—inadequate size florets—are usually made into purée for example; however there is a drop in price for this type of byproduct as compared to the calibrated florets used for freezing.

EP1597965 discloses broccoli plant suitable for mechanical harvesting that is characterized by the fact that the head of the broccoli plant is higher than the leaf canopy and furthermore that the plant does not comprise leaves having a surface area greater than about 30 square centimeters within 25 centimeters of the crown.

WO2007062009 discloses a broccoli plant having heads with detached florets arranged at the extremity of elongated secondary stems supporting said florets.

While both documents describe a broccoli plant with either exerted or detached florets, these broccoli plants are not completely suited for mechanical harvest and/or processing of individualized florets. Indeed, the broccoli plant described in EP1597965 exhibits a tight arrangement of the florets of the exerted head, an additional mechanical or manual processing of the obtained head is still necessary in order to easily obtain individualized florets.

Regarding the broccoli plant described in WO2007062009, while the florets are allegedly uniformly green and individualized, they cannot be harvested mechanically and still require manual harvesting, florettting (separation of florets from the harvested head) and trimming that does not contribute to save costs associated with the cultivation of plant suited for production of individualized florets, either for the fresh cut industry or for the frozen industry.

As an example, Tenderstem® refers to uniformly green broccoli sprouts type with an elongated stem. These products come from a variety of broccoli plant which, after cutting of the main head, produces a plurality of secondary stems with small heads at their top by sprouting. These secondary stems do not grow at the same time nor at the same speed. These sprouts need to be harvested by hand, almost one by one, and it is necessary to make a plurality of harvests over a slot of several days. All these harvesting constraints are detrimental from an economical point of view and constitute a limiting factor to the development of this particular broccoli type plant.

There is still a need for broccoli plants that produce head and/or florets that can be harvested and processed with the minimum hand-labour input in order to minimize the costs associated with the harvesting and/or processing of those heads and/or florets, particularly for the manufacture of individualized florets. The present invention aims at solving this problem and is addressing the need of providing a broccoli plant that produces a head that can be harvested by machine and florets that can also be harvested and/or processed by machine with minimal hand labor.

SUMMARY OF THE INVENTION

Accordingly, the present invention provides a cultivated broccoli plant having, at harvestable stage, a head, said head comprising a primary stem on which are branched secondary stems with florets at their top, characterized in that the florets are comprised within a plane substantially parallel to the ground.

In one embodiment, the head of the broccoli plant according to the present invention is protruding.

The invention further provides harvested broccoli head, or an assembly of heads, produced by and harvested from such broccoli plants.

In one embodiment, there is provided a broccoli head, preferably an isolated broccoli head, comprising a primary stem on which are branched secondary stems with florets at their top, characterized in that the florets are comprised within a plane substantially parallel to the ground when the head stands in the upward or upright position.

In one further embodiment, there is provided an assembly of broccoli heads, particularly isolated broccoli heads, comprising at least two broccoli heads, each comprising a primary stem on which are branched secondary stems with florets at their top, characterized in that the florets are comprised within a plane substantially parallel to the ground when the head stands in the upward position.

The expression "isolated broccoli head" means that the broccoli head is separated from the broccoli plant, ie the head has been harvested and cut-off from the plant by severing the primary stem.

The broccoli head or the assembly of plurality of broccoli heads according to the present may be assembled thanks to a food compatible packaging suitable for handling and delivering broccoli heads. Suitable packaging may be any food-approved packaging made of wood, plastic or cardboard for example. This packaging may be closed such as a bag or open such as a box for example.

Seeds for growing such broccoli plants are provided.

The present invention allows a reduction in most of the harvesting and processing issues and costs associated with them. In fact, the cultivated broccoli plant according to the present invention may comprise "multifloret" and "protruding" traits both conferring a special embodiment permitting to have all the florets arranged within one plane substantially parallel to the ground and optionally at the level or above the level of the leaf canopy. On the point of view of architecture of the head it appears that the internal secondary stems are shorter than external ones. Such architecture allows to have all florets, at the top of these secondary stems, being comprised in a plane substantially parallel to the ground.

In the present context, the expression "multifloret trait" or "multifloret" refers to a phenotypical character of the broccoli plant according to the invention which corresponds to a particular arrangement of the florets of the head. Indeed, the broccoli plant according to the present invention which has multifloret trait, ie it comprises a head comprising a primary stem on which are branched secondary stems with florets at their top, characterized in that the florets are comprised within a plane substantially parallel to the ground.

Such arrangement provides several florets of a homogeneous caliber range comprised within a horizontal plane. The broccoli heads of the broccoli plant according to the invention can therefore be qualified as flat head as compared to traditional broccoli head which are curved and convex. Such a multifloret trait is inheritable as shown in the experimental section and can thus be transferred to progeny by crossing of one broccoli parent plant that contains this trait with another broccoli parent plant that also contains it or not. The broccoli plant obtained by using at least one plant having the multifloret trait as parent will contain this multifloret trait.

In one aspect the plant according to the invention comprises a head which is protruding. The expression "protruding" or "protruding trait" means that the top of the head is at the same level than the top of the leaf canopy or that the top of the head is above the top of the leaf canopy of the plant. The canopy is the uppermost leafy level of a plant, particularly a broccoli plant. The protruding trait is a trait that can be found and obtained from a publically available broccoli plant at Oregon State University. For example lines OSU 399 or OSU 428 may be a suitable plant as source of protruding trait. The expression "above the top of the leaf canopy" it is understood that the top of the head (meaning the highest point of the head) is above the level defined by a horizontal line drawn at the very top of the leaves of the plant, ie the canopy. The top of the leaf canopy can thus be precisely defined as the individual leaf or part of leaf e.g. the tip of a leaf, which is furthest away from soil level when the plant is growing in the soil. Likewise, the bottom of the leaf canopy can be precisely defined as the leaf or part of leaf which is nearest to soil level when the plant is growing in the soil. By the expression above, it is to be understood at least 1, or at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or at least 17, or at least 18, or at least 19, or at least 20 cm and up to about 25 cm, particularly up to about 30 cm higher than the canopy.

This aspect of the plant allows the possibility of mechanical harvest avoiding the jamming of the cutting device due to the abundance of leaves. Additionally, it reduces the yellowing of florets because of better sun exposure thus resulting in a uniform color of florets and of the secondary stems holding those florets at their extremity. This "protruding trait" is inheritable and transmittable to the progeny of a plant that contains this trait. The transfer of this trait can be done by conventional crossing of broccoli plants, with at least one of the plants having the "protruding trait". A broccoli plant obtained by crossing at least one parental plant having the protruding trait will contain this protruding trait.

Plants disclosed in the present application comprise multifloret trait and protruding trait as described herein, which protruding trait and multifloret trait are obtainable from a broccoli plant designated BR51512, representative seed of which is deposited under accession Number CGMCC 4245.

DETAILED DESCRIPTION OF THE INVENTION

The present invention relates a cultivated broccoli plant exhibiting Multifloret and protruding traits.

The term "cultivated Broccoli plant" is understood within the scope of the invention to refer to a Broccoli plant that is no longer in the natural state but has been developed by human care and for human use and/or consumption. "Cultivated Broccoli plant" are further understood to exclude those wild-type species which may comprise the trait being subject of this invention as a natural trait and/or part of their natural genetics. Broccoli plant refers to species belonging to *Brassica oleracea* L convar. *Botrytis* (L), and also includes broccoli hybrids and inbred lines. Particularly, a cultivated broccoli plant is a plant that is male sterile, and more particularly a broccoli plant that comprises cytoplamic male sterility (CMS). In a particular embodiment, a cultivated broccoli plant is a broccoli plant that is resistant to disease that affects broccoli plants and that landrace and wild species are not resistant against. For example a cultivated broccoli plant in the context of the present invention may be resistant to downy mildew or may be resistant to blind eye or even resistant to both diseases.

The expression "harvestable stage" for a cultivated broccoli of the present invention refers to the mature stage of the broccoli head as usually understood by a breeder or by a grower. Such harvestable stage is typically the stage where the buds are tightly arranged and have not yet flowered, the florets are well and uniformly developed, uniformly green coloured and comprised in a plane substantially parallel to the ground.

A tight arrangement of buds at the harvestable stage can be characterised in terms of bud density. The density can be 1 bud per square millimeter (1 $mm^{-2}$), more preferably 2 $mm^{-2}$, more preferably 3 $mm^{-2}$, more preferably 4 $mm^{-2}$, most preferably 5 $mm^{-2}$.

The term "comprised in a plane substantially parallel to the ground" means that the base of the all the florets growing on a plant of the invention are almost equal distances from ground level. It is unlikely that said distances will be identical. The variation in range of measured differences in distance will preferably be no more than 5 cm, more preferably no more than 4 cm, more preferably no more than 3 cm, more preferably no more than 2 cm, more preferably no more than 1 cm, most preferably no more than 0.5 cm from ground level. For example, the height of the base of the lowest positioned floret may be 45 cm above ground level and the height of the base of the highest positioned floret may be 50 cm above ground level when growing on a plant of the invention.

The broccoli head of the plant according to the present invention has therefore, at harvestable stage, a head diameter from about 18 cm to about 30 cm, particularly from about 20 to 30 cm, more particularly from about 20 to about 26 cm, from about 20 to about 24 cm, from about 20 to about 23 cm. It will be appreciated that the head of an individual plant will not be perfectly round when viewed from above. The head diameter of an individual plant should thus be taken to mean the diameter measured at the widest point of the head when viewed from above.

As used herein, the term "about" when referring to a value or to an amount of mass, weight, length, time, or percentage is meant to encompass variations of in some embodiments ±20%, in some embodiments ±15%, and in some embodiments ±10%, in some embodiments ±5% from the specified value.

The harvestable stage corresponds to a stage where the broccoli head of the plant according to the present invention has a weight of about 200 to about 500 g, particularly from about 250 to about 500 g, more particularly from about 300 to about 450 g, even more particularly from about 300 to about 400 g, when planted at a density of about 25000 to about 50000 plants/ha, particularly from about 30000 to 40000 plants/ha. In terms of floret size, measured in equatorial diameter, the harvestable stage corresponds to a floret diameter comprised between about 30 and 60 mm for about 30 to about 70% of the florets, particularly between about 30 and 60 mm for about 40 to about 60% of the florets. Typically, the harvestable stage for broccoli corresponds to about 60 to about 70 days, particularly about 63 to about 70 days after planting when planted at a density of about 30000 to about 50000 plants/ha, particularly about 30000 to about 40000 plant/ha, under western European continental climate such as Brittany for example.

In one embodiment of the invention, head diameter and floret diameter corresponds to average head diameter and average floret diameter. The average diameter is taken to mean the average of all measured diameters of a statistically significant group of progeny plants derived from the same cross. In this case, said plants are grown at the same time and under the same conditions.

As used therein "trait" refers to characteristic or a given phenotype, for example a resistance to a disease or any phenotypic character. A trait may be inherited in a dominant or recessive manner, or may be monogenic or polygenic.

A "plant" is any plant at any stage of development, particularly a seed plant.

The expression "plant part" as used therein comprises cells, cell cultures, flowers, seeds, leaves, roots, tissues, organs, pollen, microspores, ovules or tissue cultures derived from cells of broccoli seeds or plants of the invention.

The expression "head" corresponds to the harvested part of the cultivated broccoli plant; it refers to a collection of florets attached to secondary stems, those secondary stems being arranged at the terminus of the primary stem of the broccoli plant. Head comprises one part of the primary stem, the portion of it that is above the severing point upon harvesting. The severing point is preferably anywhere between soil level and the lowest branching secondary stem, more preferably close to the lowest branching secondary stem. For the purpose of determining weight of a head, the severing point is preferably below the lowest branching secondary stem.

The expression "primary stem" as used therein, means the main stem or stalk of the broccoli plant, at the extremity of which the secondary stems start. When a broccoli head is obtained by severing, it comprises part of the primary stem on which are branched the secondary stems.

The expression "secondary stem" as is used herein, means a stem that branches from the primary stem of the broccoli plant and that is supporting—and forming part of—individual florets. A head comprises a plurality of secondary stems having florets at their top.

A "floret" refers to the flower buds cluster at the top of secondary stems and that is comprising part of that secondary stem supporting the flower bud cluster. An assembly of florets is comprised in a head. Florets provide a dense cluster of unopened and tight broccoli flowers buds.

As used herein, the phrase "trait" or "phenotypic trait" refers to the appearance or other detectable characteristic of an individual, resulting from the interaction of its genome, proteome and/or metabolome with the environment.

In one aspect of the present invention the head of the broccoli plant does not have florets deeply arranged and buried within the leaf canopy. On the contrary, the florets are comprised within a horizontal plane at the level or above the leaf canopy thus allowing the sun light to access the whole bundle of florets and secondary stems and thus conferring a uniform green color to the florets and secondary stems.

The term "uniform green color" refers to a curd or a floret having substantially no yellowing. A uniform green floret is substantially green or evenly green. Color classifications used to describe the florets are based on the color chart of the Royal Horticultural Society (RHS Color Chart). Florets of a plant of the invention are classified green and are uniform for the color (for example 137A/B, 138A/B). Florets of traditional broccoli varieties have substantial portions, often on average of at least 15% of the individual florets on a curd, which are classified as "yellow-green" (for example 144B/C, 149D-150D, and 154/B/C/B). Individual florets on traditional broccoli varieties may have as low as 10% yellowing. This color difference is based on the color of the florets (including stems) when viewed from the side after separation from the curd. The stem of the florets of traditional broccoli varieties are also often classified "yellow-green" (144 B/C and 145 B/C/D). The secondary stems of the florets of the present invention may be classified green (137A/B, 138A/B/C, and 139D). This color terminology is in accordance with The Royal Horticultural Society Colour Chart (R.H.S.C.C.) and the color descriptions refer to plate numbers in the aforementioned color chart. Color designations, color descriptions and other phenotypic descriptions may deviate from the stated values and descriptions depending upon variation in environmental, seasonal, climatic and cultural conditions. Where a color reference is given these refer to the RHS Colour Chart, The Royal Horticultural Society, London. 2001 Edition.

"Yellowing" or discoloration refers to the presence of yellow flower buds in the florets (e.g., generally at the margins) as a result of shading. A floret having substantially no yellowing refers to a floret having less than 15% yellowing as measured by the percentage of coverage across the floret having a yellow appearance. A floret having an absence of yellowing refers to a floret having less than about 5% yellowing as measured by the percentage of coverage across the floret having a more yellow than green appearance. In another aspect, florets on a curd have an average of less than about 10%, or less than about 5% yellowing as measured by the percentage of coverage across the floret having a more yellow than green appearance, yellowing can be measured at any time during the development of the florets, at harvest, or post harvest after a period of storage. In a preferred aspect, the yellowing is measured at maturity of the floret at harvest, as measured by the percentage of coverage across the floret having a more yellow than green appearance. In a preferred aspect, yellowing is measured as an average yellowing of a population of florets from a curd. In a preferred aspect, a broccoli plant of the present invention comprises a curd having an average yellowing of less than about 15%, or less than about 10%, or less than about 5% as measured by the percentage of coverage across the florets having a more yellow than green appearance.

One aspect of the present invention is the multifloret trait of the broccoli plant. This trait allows having the florets of the broccoli plant arranged in a horizontal plane within the head. Such character allows obtaining individualized florets with a minimum amount of processing and/or handling. Indeed, since the florets are not tightly arranged within a curvated plane but within a horizontal plan, a single cut below the level of florets allows getting individualized florets with minimum effort and minimum labour. Therefore the individualized florets may be obtained directly in the field by cutting at a level chosen below the plane containing those florets. Alternatively, in another embodiment, the head may be harvested in the field thanks to severing at the level of the primary stem, transported to a factory and then processed later in order to obtain individualized florets thanks to one single cut below the level of the plane containing those florets. The broccoli head according to the invention allows a much simpler and quicker processing for obtaining individualized florets. Furthermore, thanks to the arrangement of those florets substantially in the same plan, these florets are more uniform as regards to their size and green color, including the secondary stem. This allows obtaining a higher yield regarding the production of individualized florets. The broccoli head according to the present invention thus necessitates a minimal processing input either by hand or by machine and does not need any specific equipment designed for cutting florets from such a head of the broccoli plant according to the present invention.

Accordingly, there is provided a method for harvesting broccoli head comprising the steps of planting and growing a broccoli plant according to the present invention until the harvestable stage and harvesting the broccoli head by severing the primary stem.

The present invention further provides the use of a broccoli plant according to the present invention for the manufacture of broccoli heads. In one embodiment the broccoli head is packaged. A broccoli plant according to the present invention may thus be planted, grown until head formation, and the head may be harvested by severing the primary stem.

The present invention further provides the use of a broccoli plant according to the present invention for the manufacture of individualized florets. In one embodiment, the individualized florets are packaged. A broccoli plant according to the present invention may thus be planted, grown until head formation and the florets may thus be harvested by severing the secondary stem. Alternatively, the florets may be obtained by severing the secondary stem from an isolated broccoli head according to the present invention. The severing of the secondary stems in order to obtain isolated florets may be achieved in the field where the broccoli plant is grown or at any other place where the broccoli is transported to for further processing.

The size of the florets, measured in equatorial diameter, of the head of the broccoli plant according to the present invention may vary in a range comprised between about less than about 30 to more than about 60 mm.

Therefore, florets with a diameter lower than about 30 mm represent about 30 to 45%, particularly from 35% to about 45% of the total number of florets of the head, florets with a diameter comprised between about 30 and about 45 mm represent from about 20 to 40%, particularly from about 25 to 30% of the total number of floret of the head, florets with a diameter comprised between about 45 and 60 mm represent from 10 to 30%, particularly from about 15 to 35% % of the total number of the florets of the head floret with a diameter greater than about 60 mm represent from about 5 to 30%, particularly from about 5 to 25% of the total number of the florets of the head.

As described above the total number of florets of the head corresponds to the amount of florets obtained after cutting the secondary stems of the said head below the horizontal plant comprising the said florets. The term "below" as used herein before corresponds, as a matter of example, to a level comprised between the plane comprising the florets and the point of attachment of the secondary stems onto the primary stem. Typically, the cutting point below the floret is comprised between about 1 to 20 cm, particularly from about 1 to 15 cm, more particularly from about 1 to 10 cm, more particularly from about 1 to 5 cm, even more particularly from about 1 to 3 cm below the lower level of base of the florets such as illustrated in the grey rectangular zone in FIG. 1. The thus obtained florets may exhibit stem with various length as shown on FIGS. 3, 4 and 5.

From FIG. 1 and from FIG. 3, it can be inferred that the color of the secondary stem on the broccoli head according to the present invention is evenly and deeply green in term of intensity and uniformity. For comparison, on FIG. 3, a floret of a traditional broccoli head is exhibited on the left side. It can be inferred that the stem is white/creamy and that the floret is also not evenly green and shows at least 50% of yellowing.

In an embodiment, the present invention also relates to an isolated broccoli head or any assembly of a plurality of broccoli heads grown from a plant according to the invention. Such broccoli head comprises a primary stem on which are branched secondary stems with florets at their top, characterized in that the florets are comprised within a plane substantially parallel to the ground when the head is standing in the upward position.

The present invention also provides a method for producing broccoli heads comprising the steps of growing a plurality of broccoli plants according to the present invention until harvestable stage and harvesting the heads of the broccoli plants by severing the primary stem of the plant. The harvesting of the heads may be done manually of by mechanical means. Means for collecting, storing and packaging the broccoli heads are provided. The broccoli heads obtained according to the method may be fresh harvested broccoli heads ready for sale. In an alternative embodiment, the broccoli heads obtained according to the method may also be further processed.

In an embodiment, the present invention also provides a method for producing broccoli florets comprising the steps of growing a plurality of broccoli plants according to the present invention until harvestable stage and harvesting the florets of the broccoli plants by severing the secondary stem of the plant. In one embodiment, severing of the secondary stem can take place in the field by mechanical means. This is possible due to the florets being comprised within a plane substantially parallel to the ground. Accordingly, broccoli florets can be directly obtained in the field and thus do not require additional processing of handling of the broccoli head. Indeed thanks to the multifloret trait of the plant according to the present invention, broccoli florets may be directly obtained in the field since the broccoli plant allows the obtaining of individualized broccoli florets in one single cut at a predetermined level of the secondary stem. This allows great savings for both the growers and the processors of broccoli heads and florets since the florets can be directly obtained in the field and delivered either to a factory for further processing of just packed and ready for sale as fresh product.

The present invention also provide methods of transferring the multifloret trait and the protruding trait to any other broccoli plants, varieties or cultivar. The present invention is therefore not limited to one particular broccoli cultivar or variety but is applicable to all broccoli varieties. Indeed, the inventive traits of the present invention, ie multifloret trait and protruding trait, can be introgressed from any of the deposited material to any other broccoli plant by conventional breeding or by marker assisted breeding. Therefore, broccoli plants according to the present invention, having multifloret trait and protruding trait are provided. Broccoli plants according to the present invention having the protruding trait are also provided. Broccoli plants according to the present invention having the multifloret trait and the protruding trait are also provided.

The invention thus provides seed of a broccoli plant according to the invention and any plants or plant parts or progeny derived, grown or obtained from the deposited broccoli plant designated BR51512, representative seeds of which having been deposited in accordance with the Budapest Treaty at the China General Microbiological Culture Collection Center (CGMCC—No. 1 West Beichen Road—Chaoyang District—Beijing 100 101—China) under accession number CGMCC No. 4245, having a deposit date of Oct. 19, 2010.

The multifloret trait and protruding trait as disclosed in the present application are obtainable from broccoli plant designated BR51512, representative seed of which is deposited under accession Number CGMCC 4245, or from a progeny of that plant containing the multifloret trait and protruding trait obtained or derived from broccoli plant designated BR51512, representative seed of which is deposited under accession Number CGMCC 4245.

Accordingly, the man skilled in the art, based on the description of the present invention and in possession of broccoli plant designated BR51512, representative seed of which is deposited under accession Number CGMCC 4245, has no difficulty transferring the multifloret trait and protruding trait of the present invention to any other broccoli plant of various type using any breeding technique well known in the art.

The multifloret trait and the protruding trait of the present invention can be transferred to any broccoli plant lacking the multifloret trait or any broccoli plant lacking the protruding trait or any broccoli plant lacking the multifloret and the protruding trait.

The genetic information which determines the multifloret trait is obtainable from broccoli plant designated BR51512, representative seed of which is deposited under accession Number CGMCC 4245 or from a progeny of that plant comprising the trait.

The genetic information determining the protruding trait is obtainable from broccoli plant designated BR51512, representative seed of which is deposited under accession Number CGMCC 4245 or from a progeny of that plant containing the trait.

Using the teaching as disclosed herein, the genetic information determining the trait of protruding as well as the genetic information determining the trait of multifloret can be transferred to another plant, for example by crossing said plant with broccoli plant designated BR51512, representative seed of which is deposited under accession Number CGMCC 4245 or from a progeny of that deposited plant comprising both traits and determining the presence of the traits in the progeny of the cross.

Following the definition of the protruding trait and of the multifloret trait, the man skilled in the art has no difficulty to identify the plant with one or more of those traits and to follow those traits through crosses. Segregation of the traits can also be scored in the progeny resulting from the crosses.

For example, concerning the multifloret trait, the man skilled in the art has no difficulty to identify and select a broccoli plant with that trait by considering the arrangement of the florets in a plane that is substantially parallel to the ground.

Also, concerning the protruding trait, the man skilled in the art has no difficulties to identify a plant with that trait by evaluating broccoli plants and thus selecting the ones in which the top of the head is at the same level than the top of the leaf canopy or the ones in which the top of the head is above the top of the leaf canopy of the plant.

In one embodiment of the invention, a method of transferring the multifloret trait and the protruding trait according to the invention to other broccoli plants by using conventional breeding techniques and selecting progeny thereof which contains the multifloret trait and/or the protruding trait is provided. As a parental plant, for example, the broccoli plant having the genetic background of the one that has been deposited with the CGMCC can be used or any progeny from this plant provided that it contains the multifloret trait and/or the protruding trait. Such a method comprises the steps of:

providing a broccoli plant or seed which has the multifloret trait, and optionally the protruding trait, growing said plant or seed until flowering, crossing the obtained plant with a broccoli plant that does not contain multifloret trait and optionally does not contain protruding trait, optionally further crossing with the progeny of the above cross, selecting the plants which have the multiforet trait and optionally the protruding trait.

The selecting step involves the technical steps of evaluating by measurement the protrusion of the head when the protruding trait has been transferred and on the one hand and, on the other hand, evaluating the distribution of the florets of the head when the multifloret trait has been transferred.

The present invention also provides a method for producing hybrid seed of the plant according to the present invention. Such a method comprises the steps of planting rows of male and female parents of broccoli plant according to the present invention in a field, growing the plant until flowering, practicing pollination of female flowers by pollen from male flowers, and harvesting the hybrid seeds from the row of female plant.

The method may involve pollination by hand. In an embodiment the method comprises the use of male sterile, particularly cytoplasmic male sterile female inbred line in order to prevent self pollination of the female line and thus obtain 100% pure hybrid seeds.

The development of commercial broccoli hybrids involves the development of homozygous inbred parental lines through techniques well known to the art. Desirable inbred or parent lines are developed by continuous selection, followed up by several generations of selfing until the lines are sufficiently uniform. Alternatively, anther or microspore culture (followed by chromosome doubling to produce double haploids lines, also referred to as "DH" lines) may be used followed by selection of the best breeding lines and testing of progeny in various hybrid combinations.

Once the inbred lines that give the best hybrid performance have been identified, hybrid seed can be produced indefinitively, as long as the homogeneity and the homozygosity of the inbred parents is maintained. The term "inbred broccoli plant" also includes any single gene conversions of that inbred. The term "single gene converted plant" as used herein refers to those broccoli plants which are developed by a plant breeding technique called backcrossing wherein essentially all of the desired morphological and physiological characteristics of an inbred are recovered in addition to the single gene transferred from the donor parent into the inbred via the backcrossing technique.

For large scale hybrid seed production, different systems of cross pollination, based on self-incompatibility, or, alternatively, cytoplasmic male sterility (CMS), can be used. These techniques are well known in the art.

For broccoli hybrid seed production, the modem system uses CMS that was introgressed into *Brassica oleracea* from radish (Ogura, H. (1968). Studies on the new male sterility in Japanese radish, with special reference to the utilization of this sterility towards practical raising of hybrid seed (Mem Fac Agric Kagoshima Univ. 6: 39-78).

Thus, also provided is an inbred broccoli plant according to the invention which is male sterile and is suitable for being used as a female parent in hybrid seed production. In one embodiment the inbred broccoli plant is male sterile due to cytoplasmic male sterility, e.g. the ogura cms or polima cms. Such a plant can be made as known in the art.

The present invention also comprises the progeny of the broccoli plant according to the present invention as well as the progeny (obtain by selfing, by backcrossing or by crossing with an other plant) of the deposited plant which has the morphological features of the inventive plant according to the invention, ie multifloret trait and optionally protruding trait.

The present invention also concerns the use of the broccoli plant and/or head thereof for the manufacture of packaged broccoli head. Indeed the head obtained from the broccoli plant according to the invention comprises several benefits and advantages. The said head is evenly green from the stem to the florets, the florets are well individualized thanks to their arrangement within a plane and consequently the convenience for a consumer is greatly enhanced. In particular, for the cooking of broccoli, either by boiling, steaming or stir-frying, one needs to cut and individualized the florets from the head. Usually this procedure is cumbersome for most of the broccoli consumers since it requires several cutting and kitchen-processing. With the broccoli head of the plant according to the invention, the preparation of broccoli florets for cooking is drastically simplified. The consumer just needs to sever the secondary stems in one single cut and then obtain individuals floret with a minimum of processing and cutting. The individuals florets thus obtained can directly be eaten, boiled, steamed, stir-fried for example.

The present invention also concerns the use of the broccoli head thereof for the manufacture of packaged broccoli florets. Accordingly for the processing industry, the broccoli plants according to the present invention provide many benefits and advantages. The multifloret trait of the broccoli head of the present invention allows a quick and simple process for obtaining individualized florets that can be then packaged in suitable packaging for chilled or frozen marketing.

The present invention thus concerns a process for manufacturing individualized packaged broccoli florets comprising the steps of:
providing a broccoli head according to the present invention,
severing the secondary stems of the broccoli head
obtaining individualized florets
packaging the florets.

The packaging of the florets may be done with any food suitable packaging material either soft or hard. The packaged broccoli florets may be packaged with modified or non modified atmosphere in order to ensure or enhance the shelf-life of those florets.

The packaged florets may then be cooled to suitable refrigeration temperature of about 2 to 5° C. for example.

Before the packaging step, the florets can optionally be partially cooked and/or frozen according to processes well known to the man skilled in the art of food processing before being packaged and stored frozen at subzero temperature, preferably around −18° C. for example.

FIGURES

The FIG. 1 shows a broccoli head according to the present invention (BR51512) with florets comprised in a horizontal plane at the top of secondary stems.

The FIG. 2 shows a field of broccoli plants according to the invention at various maturity stages (BR51512) with protruding and multifloret heads.

The FIG. 3 shows comparison of florets of the broccoli plant according to the present invention (right hand side) with floret of conventional broccoli plant without multiforet trait (left hand side).

BRIEF DESCRIPTION OF THE PREFERRED EMBODIMENTS

Figure 1:
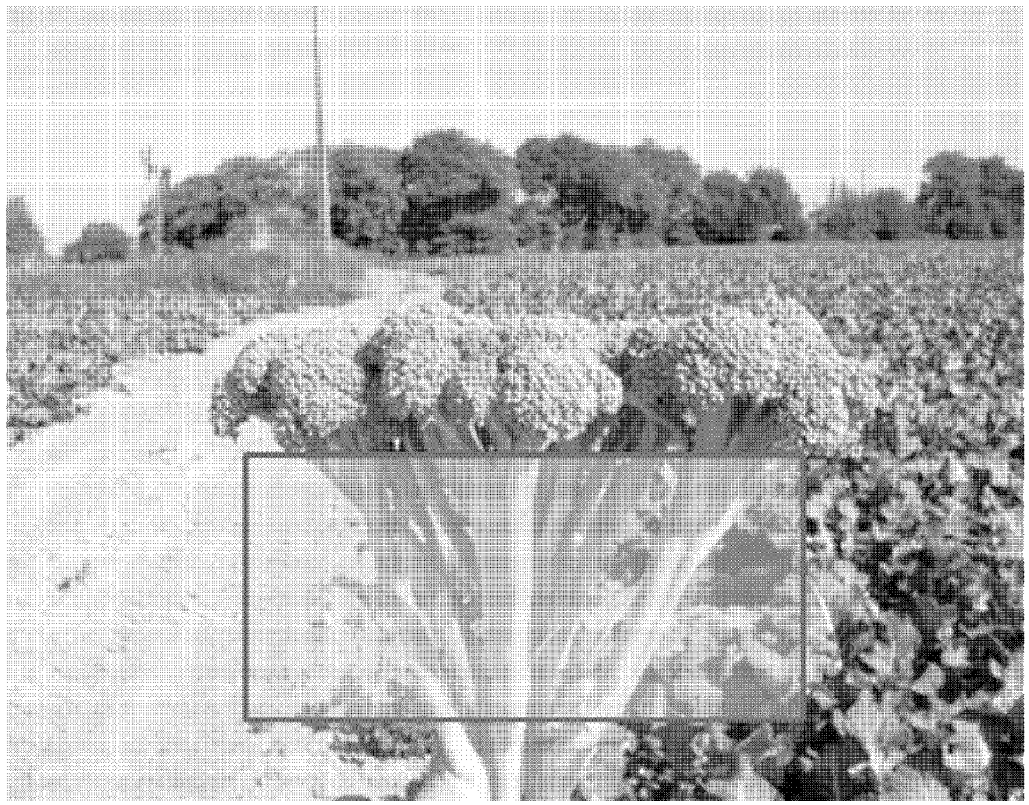

The examples below are intended to illustrate some embodiment of the present invention in a non limiting aspect.

EXAMPLES

Proprietary and public research broccoli lines were used.

For instance, the Oregon State University (OSU) broccoli breeding program had lines with moderate protruding head and separated individual florets. Several accessions were obtained from the OSU breeding program. These lines were designed as OSU 399 and OSU 428. These accessions produced low yield of processing or low quality floret separating, not multifloret trait (individualized florets but not aligned and still convex head), poor bud quality and soft individual florets. Selections for better individual floret separation led to poor bead quality and low processing yield. The present invention has found a solution to this problem to built the ideal plant type: protruding head; multifloret head; and good quality small florets after processing with satisfying yield.

In order to compensate for the defects of OSU lines and other available public lines to get 100% multifloret trait and protruding trait broccoli plants, cross designs were made and large populations were prepared for screening out plants which protruding and multifloret traits.

The screening involves more technical steps such as taking manual or visual measurements of the protrusion of the head at the level or above the canopy, measurement of the convexity if the head of the plants, measurement of the diameter and weight of broccoli heads, measurement of the weight and number of florets per head, for example. The method further comprises screening steps such as measuring the size and level of head and florets.

Example 1

Brief Breeding History of Plant
BR51512(01-7111-1/01-7229-1 x 00G028)

Female Breeding Selection

| | 01-7111 (357A/91A005(S)) Gen 2 x 01-7229 (China Long F2//Sultan F8/099) Gen 1 2001 |
|---|---|
| F1 | 2002 single plant selection |
| F2 | 2003 single plant selection |

| | |
|---|---|
| | 01-7111 (357A/91A005(S)) Gen 2 × 01-7229 (China Long F2//Sultan F8/099) Gen 1 2001 |
| F3 | 2004 single plant selection |
| F4 | 2005 single plant selection |
| F5 | 2006 selection of plant (01-7111-1/01-7229-1) |

Plant 01-7111-1/01-7229-1 originated as a result of a cross of 01-7111 (proprietary accession) with 01-7229 (proprietary accession obtained by crossing of China Long F2 with Sultan F8).

The goal was to obtain a plant combining the multifloret trait of 01-7111 with protruding trait of 01-7229.

After selection and selfing for several generations, plant 01-7111-1/01-7229-1 was selected out with suitable very good multifloret trait with florets well arranged in a plane parallel to the ground leading to flat head.

Male Breeding Selection

| | |
|---|---|
| | OSU 428 × (RB20)1-7-3/92-2684-1 2000 |
| F1 | 2001 single plant selection |
| F2 | 2002 single plant selection |
| F3 | 2003 single plant selection |
| F4 | 2004 single plant selection |
| F5 | 2005 selection of plant (00G028) |

Plant 00G028 originated as a result of a cross of OSU 428 (provided by Oregon State University) with (RBR20)1-7-3/92-2684-1 (proprietary accession). Target breeding purpose was to combine the protruding trait from OSU 428 with special traits from latter material to get novel plant which provides good compactness and protruding trait.

After selections and selfing for several generations, plant 00G028 was selected out with moderate protruding trait, and good compactness.

Breeding method used for both parents was pedigree selection, using single plant selection and mass selection practices.

Plant BR51512 Cross Making

Figure 2:

Cross was made between 01-7111-1/01-7229-1 and 00G028 in 2006, the obtained plant provides characters that make protruding trait with head situated above the leaf canopy, multifloret trait with suitable "flat head", ie florets comprised in a horizontal plane parallel to the ground (see FIG. 2), it also provides good systemic downy mildew resistance and blind eye resistance.

This clearly shows that the multifloret trait according to the invention may be transferred, introgressed, into genetic background that lacks it in order to obtain a broccoli plant according to the present invention.

The deposited plant, BR51512 can be used as a source of multifloret trait—and protruding head trait as well—for introgression in any broccoli germplasm by traditional breeding or marker assisted breeding in order to develop further broccoli plants according to the present invention (see Example 2).

Example 2

MF Breeding Scheme How to Build New MF Hybrids

It has been shown that it is possible to transfer the multifloret (MF) trait from the deposited line to more than one genetic background. In order to obtain a new MF hybrid from classic crown type lines, a cross was made between 2 new MF lines, one of which has good traits of crown type line A and the other has good traits of crown type line B.

For the development of a new MF line from crown type line A, a cross was made between the deposited MF line and a plant of crown type line A. The resulting 3 way hybrid was then backcrossed with the deposited MF line. In the BC1, plants for MF traits and good agronomic traits of line A were selected and selfed. This process was repeated a further 3 times. At the end of the process, a new fixed MF line with good traits of line A was obtained (BC1Fn). After each crossing step, broccoli plants which had a protruding head and having florets comprised within a plane substantially parallel to the ground were selected for further crossing. It was evident that the traits of protruding head and of florets being comprised within a plane substantially parallel to the ground were inherited in a simple Mendelian manner.

The same process was followed for the development of a new MF line from crown type line B.

The 2 new MF lines were then crossed to obtain a new MF hybrid which has all the features of a plant according to the present invention.

Example 3

Features of Harvested Heads and Florets

The plant BR51512 has been planted in summer at a density of 40000 plants/hectare in Brittany. This plant shows good protruding trait with head above the leaf canopy and very good multifloret trait with florets well comprised within a horizontal plane (see FIGS. 1 and 2). The heads show good compactness, the stems and florets are extremely green and well adapted to mechanical harvesting.

Broccoli heads were harvested within a harvesting frame between day 61 and day 68 after planting. The average diameter of the head was 23 cm and the average weight of the head was 350 g. The average number of florets per head was 30 and the repartition by size was the following:

45% of the florets of diameter lower than 30 mm;
30% of the florets of diameter comprised between 30 and 45 mm;
20% of the florets of diameter comprised between 45 and 60 mm;
5% of the florets of diameter above 60 mm.

Figure 3:
Figure 4:
FIG. 4 shows a plate with several florets bundles with secondary stems cut at different levels allowing to obtain different stem lengths.

From the broccoli heads grown from the broccoli plants BR51512, florets were obtained by severing the secondary stems. Short stem florets were obtained by cutting the secondary stems at the level just below the horizontal plane comprising those florets (FIG. 3 right side). Longer stem florets were obtained by cutting the secondary stems of the head at various levels getting below the florets till the insertion point of secondary stems onto primary stem (FIG. 4).

Figure 5:
FIG. 5 shows two packaged bags of broccoli florets. The photograph at the top shows packaged broccoli florets according to the invention (BR51512) and the photograph at the bottom of the page shows florets of broccoli Parthenon variety.
Figure 5:
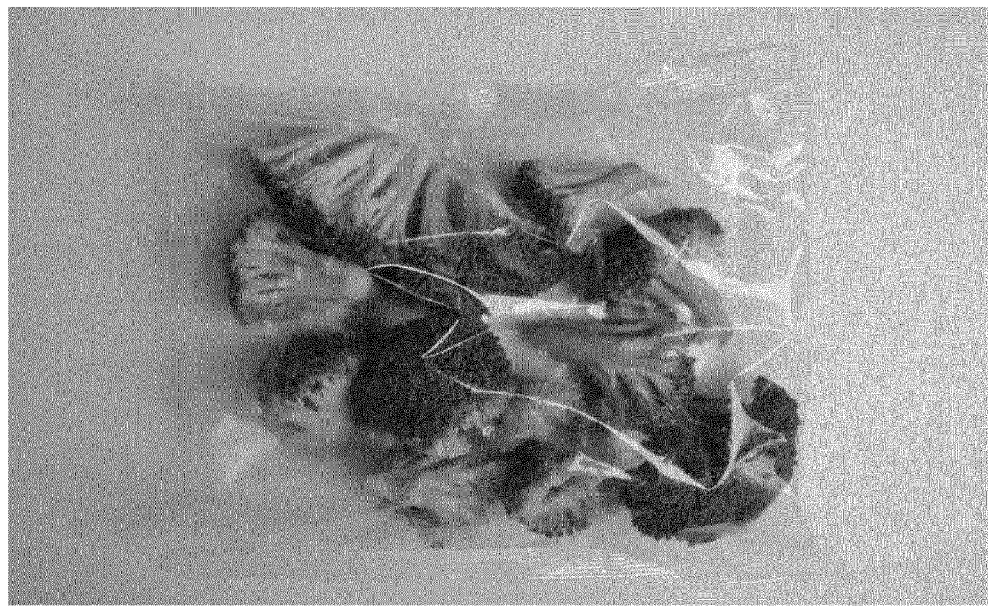

The obtained individualized florets were thus packaged in plastic bags (FIG. 5) and kept refrigerated at +4° C. for up to 9 days with quality ranked as very good to good with very slight drying visible on cut surfaces but colour still very bright. The size and green color of the florets according to the present invention are very uniform and homogeneous. Comparatively, broccoli florets from broccoli variety Parthenon were obtained, packaged and stored according to the same conditions. While the overall quality was kept equivalent to the broccoli floret according to the present invention during the storage, it can easily be seen from FIG. 5 that the color and size of the florets of Parthenon are drastically different, very heterogeneous in size and colour and much less appealing than the florets of the broccoli plant according to the present invention.

Deposit Information

Deposit of Syngenta broccoli plant BR51512 according to the invention herein disclosed has been made in accordance with the Budapest Treaty at the China General Microbiological Culture Collection Center (CGMCC—No. 1 West Beichen Road—Chaoyang District—Beijing 100 101—China) under accession number CGMCC No. 4245, having a deposit date of Oct. 19, 2010.

The invention claimed is:

1. A cultivated broccoli plant comprising a multifloret trait, said broccoli plant comprising, at harvestable stage, a head, said head comprising a primary stem on which are branched secondary stems with florets at their top, characterized in that the florets are comprised within a plane substantially parallel to the ground, wherein the variation in range of measured differences in distance to the base of all the florets growing on said plant from ground level is no more than 5 cm, and wherein the broccoli plant comprises the genetic information responsible for said multifloret trait of broccoli plant BR51512, representative seed of which was deposited with the China General Microbiological Culture Collection Center under accession number CGMCC 4245.

2. A cultivated broccoli plant according to claim 1, characterized in that the head is protruding.

3. A cultivated broccoli plant according to claim 1 characterized in that the diameter of the head is comprised from about 18 cm to about 30 cm, particularly from about 20 to 30 cm, particularly from about 20 to about 26 cm, more particularly from about 20 to about 24 cm, even more particularly from about 20 to about 23 cm.

4. A broccoli head of the cultivated broccoli plant according to claim 1, the broccoli head comprising a primary stem on which are branched secondary stems with florets at their top, characterized in that the florets are comprised within a plane substantially parallel to the ground when the head stands in the upward position.

5. A broccoli head according to claim 4, characterized in that its diameter is comprised from about 18 cm to about 30 cm, particularly from about 20 to 30 cm, more particularly from about 20 to about 26 cm, particularly from about 20 to about 24 cm, even more particularly from about 20 to about 23 cm.

6. A broccoli head according to claim 4, characterized in that its weight is comprised from about 200 to about 500 g, particularly from about 250 to about 500 g, more particularly from about 300 to about 450 g, even more particularly from about 300 to about 400 g.

7. An assembly of broccoli heads comprising at least two broccoli heads of the cultivated broccoli plant according to claim 1, each of the at least two broccoli heads comprising a primary stem on which are branched secondary stems with florets at their top, characterized in that the florets are comprised within a plane substantially parallel to the ground when the head stands in the upward position.

8. Method for harvesting a broccoli head comprising the steps of planting and growing a broccoli plant according to claim 1 until the harvestable stage and harvesting the broccoli head by severing the primary stem of the plant.

9. Method for producing broccoli heads comprising the steps of growing a plurality of broccoli plants according to claim 1 until harvestable stage and harvesting the heads of the broccoli plants by severing the primary stem of the plant.

10. Method for producing broccoli florets comprising the steps of growing a plurality of broccoli plants according to claim 1 until harvestable stage and harvesting the florets of the broccoli plants by severing the secondary stems of the plant.

11. Process for manufacturing individualized packaged broccoli florets comprising the steps of:
   a. providing a broccoli head according to claim 4,
   b. severing the secondary stems of the broccoli head,
   c. obtaining individualized florets and
   d. packaging the florets.

* * * * *